United States Patent [19]

Holland

[11] 4,163,784

[45] Aug. 7, 1979

[54] HETEROCYCLYLCARBONYL DERIVATIVES OF UREA, AGENTS FOR DISSOLUTION OF GALLSTONES

[75] Inventor: Gerald F. Holland, Old Lyme, Conn.

[73] Assignee: Pfizer Inc., New York, N.Y.

[21] Appl. No.: 884,858

[22] Filed: Mar. 9, 1978

[51] Int. Cl.$^2$ .................. A61K 31/54; A61K 31/535; A61K 31/44
[52] U.S. Cl. .................. 424/246; 424/244; 424/248.51; 424/248.54; 424/258; 424/263; 424/270; 424/272; 424/285; 260/239 B; 260/304 A; 260/304 R; 260/306.8 A; 260/306.8 D; 260/306.8 R; 260/307 H; 260/307 R; 260/347.3; 544/111; 544/124; 544/133; 544/137; 544/145; 544/152; 546/156; 546/324
[58] Field of Search .............. 424/246, 248.51, 248.54, 424/258, 263, 270, 272, 285

[56] References Cited

PUBLICATIONS

Claeson et al.-Chem. Abst., vol. 84, (1976), 30904z.
Masingale et al.-Chem. Abst., vol. 83, (1975), p. 173,166a.
Morisawa et al.-Chem. Abst., vol. 85, (1976), p. 5507k.
Pechenkin et al.-Chem. Abst., vol. 85, (1976), p. 159,606d.

*Primary Examiner*—Sam Rosen
*Attorney, Agent, or Firm*—Connolly and Hutz

[57] ABSTRACT

Heterocyclylcarbonyl derivatives of urea having the formula

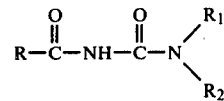

wherein R is a heterocyclyl group; $R_1$ is hydrogen, alkyl having up to ten carbon atoms or phenyl; $R_2$ is $R_1$, 1-naphthyl and phenylalkyl having 1 to 4 carbon atoms in the alkyl group; and $R_1$ and $R_2$ when taken together with the nitrogen to which they are attached are morpholino, thiomorpholino or a 6–8 membered nitrogen containing heterocyclic ring; methods for their preparation and use as agents for dissolving gallstones.

10 Claims, No Drawings

HETEROCYCLYLCARBONYL DERIVATIVES OF UREA, AGENTS FOR DISSOLUTION OF GALLSTONES

BACKGROUND OF THE INVENTION

1. Field of the Invention

This invention relates to novel heterocyclylcarbonyl derivatives of urea, to processes for making them, and to their use as agents for the dissolution of gallstones, and in particular of cholesterol gallstones.

2. Description of the Prior Art

Cholelithiasis, one of the most common diseases of Western civilization, is under intensive investigation to determine not only the physio-chemical changes in bile which lead to cholesterol gallstone formation, but also how gallstones, once formed, can be dissolved. An execellent summary of the current state of such efforts is presented by Bell in Gut, 15, 913–929 (1974).

Many attempts have been made to indirectly dissolve cholesterol gallstones by dietary manipulation or by oral administration of a compound so as to alter the composition of bile secreted by the liver and thus reverse the pathogenic process of cholelithiasis. Recently, prevention and even reversal of the pathogenic cholelithiasis process in man has been reported by the administration of chenodeoxycholic acid (U.S. Pat. Nos. 3,859,437 and 3,969,503, issued January 7, 1975 and July 13, 1976, respectively), a substance believed to inhibit synthesis of cholesterol in the body.

Various acyl derivatives of urea have been described as useful agents for lowering blood cholesterol and for other purposes. U.S. Pat. No. 4,014,876, issued Mar. 29, 1977, discloses a series of 1-(3-isoxazolylcarbonyl)ureas as hypoglycemic and/or blood free-fatty acid normalizing antidiabetic agents. Samejima, Yakugaku Zasshi, 80, 1706–12 (1960) (C.A. 55, 10439h, 1961) reports preparation of several 1-(nicotinoyl)urea derivatives as intermediates for further synthesis. Guttman, et al., J. Pharm. Sci., 56(11) 1423–7 (1967) describe 1,2-dihydro-1-methyl-2-oxoquinoxalinyl carbamyl urea, a base-catalyzed degradation product of 9-methylisoalloxazine.

U.S. Pat. No. 3,806,601, issued April 23, 1974, describes the use of bis(p-chlorophenoxy)acetylurea as a serum cholesterol and lipid lowering agent in adult animals suffering from hyperlipemia. However, a decrease in these levels by a given compound or compounds does not necessarily imply that reversal of the pathogenic process of cholelithiasis with indirect solubilization of cholesterol gallstones will occur. U.S. Pat. No. 3,245,878, issued Apr. 12, 1966, reports on several acyl(alkanoyl, aroyl)-3-benzyloxyureas as agents for lowering blood cholesterol.

South African Pat. No. 7,501,773, published Jan. 13, 1976, describes 1-furoyl-3-(3-chloro-4-methylphenyl)-2-thiourea, a compound useful for controlling the ripening of sugar cane. Several N-carbamoylpyrazinecarboxamides useful as diuretics are described in U.S. Pat. No. 3,345,372, issued Oct. 3, 1967.

SUMMARY OF THE INVENTION

It has now been found that heterocyclylcarbonyl ureas having the formula

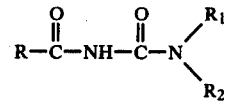

wherein R is selected from the group consisting of
pyridyl,
chlorosubstituted pyridyl,
quinolyl,
furyl,
5-methyl-3-isoxazolyl,
3-methyl-5-isoxazolyl,
3-methyl-5-isothiazolyl,
4-methyl-5-thiazolyl,
4-methyl-5-oxazolyl,
5-methyl-3-phenyl-4-isoxazolyl,
isothiazolyl,
3-(1,2,5-thiadiazolyl),
4-(1,2,3-thiadiazolyl),
3-(1,2-benzisothiazolyl) and
thiazolyl;
$R_1$ is selected from the group consisting of hydrogen, alkyl having from one to ten carbon atoms and phenyl;
$R_2$ is selected from the group consisting of $R_1$, 1-naphthyl and phenylalkyl wherein the alkyl has from one to four carbon atoms;
$R_1$ and $R_2$ when taken together with the nitrogen to which they are attached are selected from the group consisting of
morpholino,
thiomorpholino,
1-(1,2,3,6-tetrahydropyridyl),
1-azacycloheptyl,
1-azacyclooctyl,
3-(2,3,4,5-tetrahydro-3,1-benzazepinyl) and

wherein Z is selected from the group consisting of hydrogen, alkyl having from one to four carbon atoms, alkoxy having from one to four carbon atoms, chloro and phenylalkyl having from one to four carbon atoms in the alkyl group,
and the pharmaceutically acceptable acid addition salts of those compounds wherein R is a basic group are valuable agents for the dissolution of cholesterol gallstones in mammals, including humans. Additionally, they reduce biliary lipid pools in mammals.

Also included in this invention are the pharmaceutically acceptable acid addition salts of those compounds wherein R is a basic group, e.g. pyridyl. Representative of such salts are the hydrochloride, hydrobromide, sulfate, phosphate, pamoate, citrate, malate, fumarate, tartrate, glycolate, maleate, p-toluenesulfonate, succinate, oxalate, mandelate, acetate and lactate. Such salts are prepared by known procedures.

The favored compounds of this invention are those wherein $R_1$ and $R_2$ together with the nitrogen to which they are attached represent a ring structure, especially a 6-membered ring, and those wherein $R_1$ when taken individually is hydrogen and $R_2$ when taken individually is phenylalkyl. Preferred compounds are those favored compounds wherein $NR_1R_2$ represents 1-(1,2,3,6-tetrahydropyridyl) and $NHCH_2C_6H_5$ and R is pyridyl, chloro substituted pyridyl or 3-quinolyl.

DETAILED DESCRIPTION OF THE INVENTION

The compounds of this invention are readily prepared by reaction of the appropriate hetercyclylcarbonyl isocyanate [R—CO—N=C=O] with desirably an excess of an appropriate amine of formula $HNR_1R_2$ in a reaction-inert solvent at a temperature of from about 0° C. to about 100° C. (Method A). The favored temperature range is from about 20° C. to about 50° C. since the reaction proceeds satisfactorily within this temperature range as regards reaction rate and yield of product. Alternatively, they can be prepared by reacting the appropriate hetercyclylcarboxamides [R—CONH$_2$] with an appropriate isocyanate (R$_2$—N=C=O) under conditions similar to those described above. This latter procedure, of course, affords products having only one substituent (R$_2$) on the terminal nitrogen of the desired product. Representative solvents for these reactions are methylene chloride, ethylene dichloride, tetrahydrofuran, dioxane, diethyl ether, dimethyl ether of ethylene glycol, benzene, toluene and xylene.

A further procedure comprises reacting the appropriate 1-heterocyclyl-3,3-diphenylurea with an appropriate amine (HNR$_1$R$_2$) in a reaction-inert solvent at an elevated temperature in the presence of an acid (Method B). Temperatures of from about 50° C. to about 200° C. are suitable for the reaction. The favored range is from about 85° C. to about 150° C. Suitable solvents for this procedure are those enumerated above, the boiling points of which fall within the temperature range cited.

The presence of an acid expedites the reaction. The acid can be added separately to the reaction mixture or can be added as an acid addition salt of the amine reactant. The acid and amine are generally used in equimolar ratios. The ratio of acid to amine, however, is not critical but can vary from trace amounts of acid to up to several molar excesses. The favored ratio of acid to amine is from about 2:1 to about 1:2.

A still further procedure comprises acylation of a urea derivative of the formula $H_2N$—CO—$NR_1R_2$ with an appropriate heterocyclyl acid chloride R—COCl in a reaction-inert solvent, that is, a solvent which does not react to any appreciable extent with the reactants or products. Suitable solvents include alkanols having from one to four carbon atoms, halogenated hydrocarbons such as methylene chloride, chloroform, carbon tetrachloride, and hydrocarbons such as benzene, toluene, xylene, n-hexane, and cyclohexane. An acid acceptor is also used. Representative acid acceptors for use in the above solvent systems are tertiary organic bases such as triethylamine, pyridine, collidine picoline and alkali metal alkoxides. Water can also be used as solvent since reaction occurs primarily and preferentially with the urea reactant. When using water as solvent, typical Schotten-Baumann reaction conditions are employed. Regardless of the solvent system used, the reaction is usually conducted at a temperature of from about 10° C. to about 100° C.

Another suitable procedure comprises reacting a lower alkyl ester of a heterocyclic carboxylic acid R—COOR° wherein R is as previously defined and R° is lower alkyl having up to four carbon atoms with the sodium (or potassium) salt of an appropriate urea reactant of the formula $NaHN$—CO—$NR_1R_2$ in a reaction-inert solvent such as chloroform, N,N-dimethylformamide, toluene and tetrahydrofuran at a temperature of from about $-10°$ C. to about 70° C.

The requiste isocyanates of formula R—CO—N=C=O are conveniently prepared by reaction of the corresponding amide with oxalyl chloride in a reaction-inert medium such as ethylene dichloride, xylene, toluene, at temperatures from about 0° C. to about 100° C. A slight excess, up to 10%, of oxalyl chloride is generally used to insure complete reaction of the amide. The isocyanate need not be isolated from the reaction mixture. In actual practice, it has been found most convenient to add the amine reactant $HNR_1R_2$ directly to the isocyanate containing reaction mixture.

When the isocyanate reactants are of the formula $R_2$—N=C=O, they are prepared by reaction of the appropriate primary amine $R_2NH_2$ with phosgene under reaction conditions similar to those described above.

The amide reactants used to prepare the isocyanate reactants described above are in turn prepared from the corresponding nitriles by hydrolysis according to known procedures. A convenient procedure comprises reaction of the nitrile with an alkali metal hydroxide, e.g., potassium hydroxide, and hydrogen peroxide in a solvent such as ethanol at temperatures from about room temperature to the reflux temperature until evolution of gas is complete. Alternatively, they are prepared by amidation of the corresponding acid chlorides according to well known procedures. The acid chlorides are prepared by reaction of the appropriate carboxylic acid with thionyl chloride, the latter generally serving as reactant and solvent.

The compounds described herein are useful in dissolving gallstones in mammals and, when used for such purpose, are administered orally or parenterally in unit dosage form either alone or in the form of pharmaceutical preparations; that is, in combination with other therapeutic agents and/or a pharmaceutically acceptable carrier, the latter selected on the basis of the chosen route of administration and standard pharmaceutical practice. For example, they can be combined with various pharmaceutically-acceptable inert carriers in the form of tablets, capsules, lozenges, troches, hard candies, powders, aerosol sprays, aqueous suspensions or solutions, injectable solutions, elixirs, syrups and the like. Such carriers include solid diluents or fillers, sterile aqueous media and various non-toxic organic solvents. Moreover, the oral pharmaceutical compositions of this invention can be suitably sweetened and flavored by means of various agents of the type commonly used for this purpose.

The particular carrier selected and the proportion of active ingredient to carrier are influenced by the solubility and chemical nature of the therapeutic compounds, the chosen route of administration and the needs of standard pharmaceutical practice. For example, when the compounds of this invention are administered orally in tablet form, excipients such as lactose, sodium citrate, calcium carbonate and dicalcium phosphate can be used. Various disintegrants such as starch, alginic acids and certain complex silicates, together with lubricating agents such as magnesium stearate, sodium lauryl sulphate and talc, can also be used in producing tablets for the oral administration of these compounds. For oral administration in capsule form, lactose and high molecular weight polyethylene glycols are among the preferred materials for use as pharmaceutically-acceptable carriers. Where aqueous suspensions are to be used for oral administration, the compounds of this invention can be combined with emulsifying or suspending agents. Diluents such as ethanol, propylene glycol, glycerine and chloroform and their combinations can be employed as well as other materials.

For the purpose of parenteral administration, solutions or suspensions of these compounds in sesame or peanut oil or in aqueous propylene glycol solutions can be employed, as well as sterile aqueous solutions of the soluble pharmaceutically-acceptable salts described herein. These particular solutions are especially suited for intramuscular and subcutaneous injection purposes should such method of administration be desired. The aqueous solutions, including those of the salts dissolved in pure distilled water, are also useful for intravenous injection purposes provided that their pH is properly adjusted beforehand. Such solutions should also be suitably buffered, if necessary, and the liquid diluent first rendered isotonic with sufficient saline or glucose.

It is necessary that the active ingredient form a proportion of the composition such that a suitable dosage form will be obtained. Obviously, several dosage unit forms can be administered at about the same time. Although compositions with less than 0.005% by weight of active ingredient might be used in certain instances, it is preferred to use compositions containing not less than 0.005% of the active ingredient; otherwise, the amount of carrier becomes excessively large. Activity increases with the concentration of the active ingredient. The composition may contain 10, 50, 75, 95 or an even higher percentage by weight of the active ingredient.

The dosage unit administered can be any gallstone dissolving effective amount. Dosages of from about 10 mg./kg. to about 100 mg./kg. per day, and preferably from about 10 mg./kg. to about 50 mg./kg. per day are effective in achieving the desired effect.

In addition to the above mentioned methods of administration, the compounds of this invention can be administered by intraductal infusion, a method of considerable value in the treatment of patients having stones retained in the common bile duct after cholecystectomy and common duct exploration. It is of particular value in situations where the gallstones are between the T-tube and the duodenum. A convenient dosage form for this method is a saline solution buffered to pH 7.5. Concentrations of from about 10 millimoles to about 200 millimoles of the chosen compound are practical for such use. The solutions are allowed to drip into the duct at a rate of 30 ml. per hour for periods of from 3 to 14 days.

The value of the herein-described compounds as agents for the dissolution of gallstones arises from their ability to decrease the lithogenic index; i.e., the relative concentrations of the three major bile lipids: cholesterol, bile acids and phospholipids. It expresses the cholesterol level as a percentage of the concentration that would be required to saturate bile of that particular bile acid and phospholipid concentration or, it is 100 times the ratio of cholesterol actually present to the maximal amount that would be soluble at the phospholipid-bile acid ratio of a given sample.

The effects of the compounds described herein, and their efficacy are dependent upon their increase in bile acid synthesis in vivo. The compounds increase the conversion of cholesterol to bile acids by increasing the activity of the rate-controlling enzyme, cholesterol 7α-hydroxylase. The direct measurement of bile acid synthesis in vivo and, hence, the determination of the ability of these compounds to dissolve gallstones is accomplished according to the procedure of Sjovall, Meth. Biochem. Anal., 12, 123 (1964). In this procedure, male albino mice, weight ca. 25 gm., are adapted to a synthetic diet (sucrose, casein, corn oil, salts and vitamins) for 1-2 weeks. They are then fed the test compounds mixed into their diet (maximum 0.15%) for 4 days. One day before sacrifice (3 days on drug), the mice are injected i.p. with 0.2 ml. of solution containing (in 35 ml.) 10 μc $^3$H-cholic acid, 50 μc $^{14}$C-cholesterol (both carrier free), 2% bovine serum albumin, and 0.9% NaCl. Food consumption and initial and final body weights are recorded for each group. The animals are sacrificed 24 hours after injection by decapitation and exsanguination. The small intestine of each animal is removed, and its contents rinsed into a screw-cap 30-ml. polypropylene tube with 10 ml. saline. Saturated KOH (2.5 ml.) and carrier taurodeoxycholate are added to each tube, and the tubes autoclaved at 15 psi for 4 hours. The contents are acidified with 4 ml. conc. HCl and extracted with 2×15 ml. ethyl acetate. The extracts are combined, dried over anhydrous granular sodium sulfate, and evaporated under nitrogen. The residue is treated with excess diazomethane in ether-methanol, re-dried, and dissolved in a small volume of chloroform. Samples are streaked on silica gel GF thin layer chromatography plates (Analtech, 5 cm. lanes), developed in acetone-benzene (2:3), and stained with $I_2$ vapor. Two bands are located according to standards (C, cholate, and D, dihydroxy bile acids) and scraped into scintillation vials containing 1 ml. ethanol. Ten ml. of triton-toluene scintillation fluid (1:2, 40 gm. Omnifluor per liter) are added; radioactivity and external standard ratio are determined (Beckman LS-230, narrow $^3$H and $^{14}$C channels). Alternatively, C-band scrapings are mixed with 1.0 ml. iso-propanol and centrifuged; cholate is determined in duplicate 0.10 ml. samples of supernatant; the remainder, including residual silica gel, is counted. Calculations are performed by PDP-10 computer program. Untreated controls are run daily, and positive controls at frequent intervals (2% cholestyramine is run as standard). [Omnifluor is a blend of 98% 2,5-diphenyloxazole and 2% p-bis-(o-methylstyryl)benzene, available from New England Nuclear Corp., Boston, Massachusetts, U.S.A.].

Several of the compounds described herein, but by no means all, have exhibited toxic effects when administered to animals at high doses. For example, oral administration of 6-chloro-N-[1-(1,2,3,6-tetrahydropyridyl)-carbonyl]nicotinamide to dogs at 250 mg./kg., ten times the projected efficacious dose, resulted in death of the dogs, with pathological signs suggestive of cardiac impairment. Administration of this agent at the same high dose to rats caused only moderate toxicological symptoms, including lethargy, diminished appetite and weight gain, and slight abnormalities in clinical chemistry.

The compounds were tested for acute toxicity in the following manner. Healthy male CD-1 mice (20-25 g.), 10 mice per group, received a single high dose of drug by intraperitoneal administration (1000 mg./kg., in 0.6% Tween 20, at a concentration of 70 mg./ml.). (Tween 20, polyoxyethylene sorbitan monolaurate, available from Atlas Chemical Industries, Inc.). The animals were observed continuously for at least two hours, again at 24 hours and daily thereafter for one week. Controls received vehicle alone, 1.43 ml./kg. and were asymptomatic throughout. The compounds tested and the widely varying mortality rates observed are tabulated below.

$$R-\overset{O}{\underset{\|}{C}}-NH-\overset{O}{\underset{\|}{C}}-N\overset{R_1}{\underset{R_2}{\diagdown}}$$

| R | $NR_1R_2$ | Mortality Rate |
|---|---|---|
| 6-chloro-3-pyridyl | 1-(1,2,3,6-tetrahydro-pyridyl) | 0/10 |
| 3-pyridyl | 1-(1,2,3,6-tetrahydro-pyridyl) | 9/10 |
| 5-thiazolyl | $N$-$(n$-$C_4H_9)_2$ | 4/10 |
| 2-chloro-3-pyridyl | $NH(CH_2C_6H_5)$ | 0/10 |
| 3-pyridyl | $N$-$(n$-$C_4H_9)_2$ | 10/10 |

In seven-day chronic toxicity tests on healthy male CD-1 mice, 5 mice per group, daily doses of 500 mg./kg. orally in 0.1% methyl cellulose for 5 days, 6-chloro-N-[1-(1,2,3,6-tetrahydropyridyl)carbonyl]-nicotinamide produced hepatotoxicity. On the other hand, 2-chloro-N-(benzylaminocarbonyl)nicotinamide and 3-{N-[(1,2,3,6-tetrahydropyridyl)carbonyl]}-quinoline carboxamide showed no hepatotoxicity in the same test at the same high doses.

Despite the observation of toxicity of certain of the compounds of this invention at high dose levels in certain animal species; that is, at dose levels ten times the projected efficacious dose, said compounds are effective and useful for dissolving cholesterol gallstones in mammals at dose levels substantially below those at which toxicity is observed.

EXAMPLE 1

6-Chloro-N-[1-(1,2,3,6-tetrahydropyridyl)carbonyl]-nicotinamide

To a solution of 6-chloronicotinamide (3.13 g., 0.020 mole) in dry ethylene dichloride (75 ml.) under a nitrogen atmosphere is added oxalyl chloride (2.86 g., 0.022 mole) and the resulting suspension stirred and heated at 85° C. for 90 minutes. The reaction mixture, now a clear solution, is cooled to 20° C. Then, 1,2,3,6-tetrahydropyridine (7.32 g., 0.088 mole) is added dropwise, with stirring, at such a rate as to maintain a temperature of 20°-30° C. Upon completion of addition, the mixture is stirred an additional half hour at room temperature. Hexane (150 ml.) is added and the mixture extracted with 1 N sodium hydroxide (100 ml.) and then with water (100 ml.). The extracts are combined, filtered and acidified with acetic acid to pH 5.5. The crystalline product which precipitates is filtered, oven dried at 70° C. Yield 4.80 g. (90.3%); m.p. 152°-154° C. Upon recrystallization from hot ethyl acetate and drying, the product melts at 158°-159.5° C. Yield 4.085 g.

Analysis: Calc'd. for $C_{12}H_{12}O_2N_3Cl$: C, 54.24; H, 4.55; N, 15.81%; Found: C, 54.30; H, 4.33; N, 16.12%.

EXAMPLE 2

N-(Hexamethyleneiminocarbonyl)isonicotinamide

A mixture of isonicotinamide (2.45 g., 0.02 mole), tetrahydrofuran (250 ml.) and oxalyl chloride (2.08 ml., 0.024 mole) is refluxed under a nitrogen atmosphere for 3.5 hours and is then cooled to room temperature. Hexamethyleneimine (9 ml., 0.08 mole) is added and the reaction stirred for one hour at room temperature. Benzene (200 ml.) is added and the resulting mixture extracted with water (50 ml.). The extract contains largely isonicotinamide. The reaction mixture is extracted with 1 N sodium hydroxide (50 ml.), the extract acidified with acetic acid and then extracted with ethyl acetate. Concentration of the ethyl acetate extract affords 0.7 g. of oil which crystallizes from ethyl acetate-hexane (1:1). Yield 128 mg. (2.6%); m.p. 125°-127° C.

Analysis: Calc'd. for $C_{13}H_{17}O_2N_3$: C, 63.14; H, 6.93; N, 16.99%; Found: C, 63.03; H, 6.92; N, 17.07%.

EXAMPLE 3

N-(Di-isopentylaminocarbonyl)nicotinamide

To a mixture of nicotinamide (24.4 g., 0.20 mole) and dry ethylene dichloride (2500 ml.) is added oxalyl chloride (38.1 g., 0.30 mole). The mixture is then heated to reflux for 4.5 hours and then cooled to room temperature. It is filtered to give a clear pale orange solution of nicotinyl isocyanate which is used directly in the next step.

Over a ten minute period a solution of diphenylamine (50.7 g., 0.30 mole) in dry ethylene dichloride (100 ml.) is added to the isocyanate solution. A precipitate forms immediately and the suspension is stirred at room temperature for an additional half hour. The reaction mixture is filtered, the filter cake washed with ether and air dried. It is slurried in ether (2000 ml.), filtered and dried. Yield=39 g. m.p. 141°-146° C. The dry crystals are dissolved in 1 N sodium hydroxide (350 ml.), immediately filtered and the filtrate acidified with glacial acetic acid. The off-white precipitate of N-(diphenylaminocarbonyl)nicotinamide is filtered and dried at 50° C. Yield=26.3 g. (42%); m.p. 142°-145° C.

A mixture of N-(diphenylaminocarbonyl)nicotinamide (1.6 g., 0.005 mole), toluene (50 ml.), diisopentylamine (2.4 g., 0.015 mole) and glacial acetic acid (0.86 ml.) is heated and stirred at 95°-97° C. for one hour. The mixture is cooled to room temperature and extracted with 1 N sodium hydroxide (50 ml.). The extract is acidified with glacial acetic acid and the oil which separates extracted with ethyl acetate. Evaporation of the extract under reduced pressure gives 1.9 g. of oil. The oil is taken up in ether (20 ml.), the solution made acid with ethyl acetate-HCl and then diluted with an equal volume of hexane to precipitate a gum. Trituration of the gum with acetone (10 ml.) affords the crystalline product. Yield=1.04 g. (61%); m.p. 112°-115° C.

Analysis: Calc'd. for $C_{17}H_{27}O_2N_3 \cdot HCl$: C, 59.72; H, 8.25; N, 12.29%; Found: C, 59.29; H, 8.15; N, 12.43%.

EXAMPLE 4

The following compounds are prepared from appropriate reactants according to the procedures of Examples 1, 2 or 3.

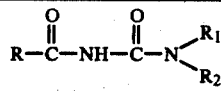

| R | NR₁R₂ | M.P. (°C.) | Method of Example |
|---|---|---|---|
| 3-pyridyl | $NH_2$ | 223–228 | 1 |
| 3-pyridyl | $NH(CH_3)$ | 222–223(a) | 1 |
| 3-pyridyl | $NH(C_2H_5)$ | 195–197(a) | 1 |
| 3-pyridyl | $NH(CH_2)_5CH_3$ | 76–77 | 3 |
| 3-pyridyl | $NH(CH_2)_9CH_3$ | 66–68 | 3 |
| 3-pyridyl | $N(CH_3)_2$ | 90–92 | 1 |
| 3-pyridyl | $N(n-C_3H_7)_2$ | 138–140(a) | 1 |
| 3-pyridyl | $N(n-C_4H_9)_2$ | 112–115(a) | 2 |
| 3-pyridyl | $N[(CH_2)_2CH(CH_3)_2]_2$ | 112–115(a) | 3 |
| 3-pyridyl | $N[CH_2CH(CH_3)_2]_2$ | 143–147(a) | 2 |
| 3-pyridyl | piperidino | 162–164 | 1 |
| 3-pyridyl | 4-methylpiperidino | 105–108 | 1 |
| 3-pyridyl | 4-(n-propyl)piperidino | 121–123 | 1 |
| 3-pyridyl | 4-(3-phenylpropyl)piperidino | 93–96 | 1 |
| 3-pyridyl | 4-chloropiperidino | 118–120 | 1 |
| 3-pyridyl | 4-benzylpiperidino | 121–122 | 1 |
| 3-pyridyl | thiomorpholino | 179–181 | 1 |
| 3-pyridyl | 3-methylpiperidino | 143–145 | 1 |
| 3-pyridyl | morpholino | 165–166 | 1 |
| 3-pyridyl | 1-azacycloheptyl | 136–138 | 1 |
| 3-pyridyl | 1-azacyclooctyl | 93–96 | 1 |
| 3-pyridyl | 3-(2,3,4,5-tetrahydro-3,1-benzazepinyl) | 155–517 | 1 |
| 3-pyridyl | 1-(1,2,3,6-tetrahydropyridyl) | 171–173(a) | 3 |
| 3-pyridyl | $NH(C_6H_5)$ | 223–226(a) | 3 |
| 3-pyridyl | $NH(C_6H_{11})$ | 145–146 | 1 |
| 3-pyridyl | $NH(CH_2C_6H_5)$ | 156–518 | 2 |
| 3-pyridyl | NH(1-naphthyl) | 232–235(a) | 3 |
| 3-pyridyl | $NH(n-C_4H_9)$ | 98–100 | 2 |
| 4-pyridyl | $NH(CH_3)$ | 220–222 | 2 |
| 4-pyridyl | $NH(C_2H_5)$ | 172–175 | 2 |
| 4-pyridyl | $NH(n-C_4H_9)$ | 107–109 | 2 |
| 4-pyridyl | $NH(CH_2)_5CH_3$ | 78–81 | 2 |
| 4-pyridyl | $N(CH_3)_2$ | 165–167 | 2 |
| 4-pyridyl | $N(n-C_3H_7)_2$ | 138–141 | 2 |
| 4-pyridyl | $N[(CH_2)_2CH(CH_3)_2]_2$ | 150–155 | 2 |
| 4-pyridyl | $N(n-C_4H_9)_2$ | 220 (dec.) | 2 |
| 4-pyridyl | piperidino | 143–145 | 3 |
| 4-pyridyl | 1-(1,2,3,6-tetrahydropyridyl) | 117–119 | 1 |
| 4-pyridyl | 1-azacycloheptyl | 125–127 | 2 |
| 5-chloro-3-pyridyl | 1-(1,2,3,6-tetrahydropyridyl) | 133–135 | 1 |
| 6-chloro-3-pyridyl | $NH_2$ | 244–246 | 1 |
| 6-chloro-3-pyridyl | $NH(CH_3)$ | 235–237 | 1 |
| 6-chloro-3-pyridyl | $NH(n-C_4H_9)$ | 172–174 | 1 |
| 6-chloro-3-pyridyl | $NH(CH_2)_5CH_3$ | 143–145 | 1 |
| 6-chloro-3-pyridyl | $NH(CH_2)_6CH_3$ | 143–145 | 1 |
| 6-chloro-3-pyridyl | $NH(CH_2C_6H_5)$ | 191–192 | 1 |
| 6-chloro-3-pyridyl | $NH(C_6H_{11})$ | 220–222 | 1 |
| 6-chloro-2-pyridyl | $N(CH_3)_2$ | 121–123(b) | 1 |
| 6-chloro-3-pyridyl | $N(n-C_3H_7)_2$ | 87–89(b) | 1 |
| 6-chloro-3-pyridyl | $N(n-C_4H_9)_2$ | 123–125(b) | 1 |
| 6-chloro-3-pyridyl | piperidino | 150–152 | 1 |
| 6-chloro-3-pyridyl | morpholino | 144–146 | 1 |
| 6-chloro-3-pyridyl | 3-methylpiperidino | 115–116 | 1 |
| 6-chloro-3-pyridyl | thiomorpholino | 143–145 | 1 |
| 6-chloro-3-pyridyl | 4-(3-phenylpropyl)piperidino | 138–140 | 1 |
| 6-chloro-3-pyridyl | 2-methylpiperidino | 143–145 | 1 |
| 6-chloro-3-pyridyl | 1-azacycloheptyl | 108–110 | 1 |
| 6-chloro-3-pyridyl | 1-azacyclooctyl | 117–119 | 1 |
| 6-chloro-3-pyridyl | 4-chloropiperidino | 157–159 | 1 |
| 6-chloro-3-pyridyl | 4-(n-propyl)piperidino | 130–132 | 1 |
| 6-chloro-3-pyridyl | 4-benzylpiperidino | 152–154 | 1 |
| 6-chloro-3-pyridyl | 3-(2,3,4,5-tetrahydro-3,1-benzazepinyl) | 170–172 | 1 |
| 6-chloro-3-pyridyl | $N[CH_2CH(CH_3)_2]_2$ | 108–110 | 1 |
| 6-chloro-3-pyridyl | $N[(CH_2)_2CH(CH_3)_2]_2$ | 69–71 | 1 |
| 6-chloro-3-pyridyl | 4-methylpiperidino | 137–139 | 1 |
| 6-chloro-3-pyridyl | $N[CH(CH_3)CH_2CH_3]_2$ | 142–144 | 1 |
| 6-chloro-2-pyridyl | $NH_2$ | 273–275 | 1 |
| 6-chloro-2-pyridyl | $NH(n-C_4H_9)$ | 108–110 | 1 |
| 6-chloro-2-pyridyl | $NH(CH_2)_9CH_3$ | 90–92 | 1 |
| 6-chloro-2-pyridyl | $NH(CH_2C_6H_5)$ | 190–191 | 1 |
| 6-chloro-2-pyridyl | $N(CH_3)_2$ | 207–209 | 1 |
| 6-chloro-2-pyridyl | piperidino | 155–156 | 1 |
| 6-chloro-2-pyridyl | 1-(1,2,3,6-tetrahydropyridyl) | 115–116 | 1 |
| 6-chloro-2-pyridyl | $N(n-C_4H_9)_2$ | 81–83 | 1 |
| 3-quinolyl | $NH(C_2H_5)$ | 222–224 | 1 |
| 3-quinolyl | $NH(n-C_4H_9)$ | 164–166 | 1 |

-continued $$R-\overset{O}{\underset{\|}{C}}-NH-\overset{O}{\underset{\|}{C}}-N\overset{R_1}{\underset{R_2}{}}$$

| R | NR₁R₂ | M.P. (°C.) | Method of Example |
|---|---|---|---|
| 3-quinolyl | N(n-C₄H₉)₂ | 108–110 | 1 |
| 3-quinolyl | N[CH₂CH(CH₃)₂]₂ | 141–143 | 1 |
| 3-quinolyl | 1-azacycloheptyl | 146–148 | 1 |
| 3-quinolyl | 4-benzylpiperidino | 188–190 | 1 |
| 3-quinolyl | 2-methylpiperidino | 142–144 | 1 |
| 3-quinolyl | piperidino | 152–154 | 2 |
| 3-quinolyl | 1-(1,2,3,6-tetrahydropyridyl) | 157–159 | 2 |
| 5-quinolyl | piperidino | 190–193 | 2 |
| 3-methyl-5-isoxazolyl | NH₂ | 264–265 | 1 |
| 3-methyl-5-isoxazolyl | NH(C₂H₅) | 199–200 | 1 |
| 3-methyl-5-isoxazolyl | N(CH₃)₂ | 112–113 | 1 |
| 3-methyl-5-isoxazolyl | N(n-C₃H₇)₂ | 79–80 | 1 |
| 3-methyl-5-isoxazolyl | NH(C₆H₅) | 206–207 | 1 |
| 3-methyl-5-isoxazolyl | piperidino | 121–122 | 1 |
| 3-methyl-5-isoxazolyl | morpholino | 125–126 | 1 |
| 3-methyl-5-isoxazolyl | thiomorpholino | 162–164 | 1 |
| 3-methyl-5-isoxazolyl | 4-chloropiperidino | 180–182 | 1 |
| 3-methyl-5-isoxazolyl | 4-methoxypiperidino | 113–115 | 1 |
| 3-methyl-5-isoxazolyl | 4-benzylpiperidino | 128–130 | 1 |
| 3-methyl-5-isoxazolyl | 3-methylpiperidino | 121–123 | 1 |
| 3-methyl-5-isoxazolyl | 4-methylpiperidino | 115–116 | 1 |
| 3-methyl-5-isoxazolyl | 2-methylpiperidino | 118–119 | 1 |
| 3-methyl-5-isoxazolyl | 4-n-propylpiperidino | 127–129 | 1 |
| 3-methyl-5-isoxazolyl | 1-azacycloheptyl | 114–116 | 1 |
| 3-methyl-5-isoxazolyl | 1-azacyclooctyl | 108–110 | 1 |
| 3-methyl-5-isoxazolyl | 4-(3-phenylpropyl)piperidino | 116–118 | 1 |
| 3-methyl-5-isoxazolyl | 1-(1,2,3,6-tetrahydropyridyl) | 103–105 | 1 |
| 3-methyl-5-isoxazolyl | 3-(2,3,4,5-tetrahydro-3,1-benzazepinyl) | 150–152 | 1 |
| 5-methyl-3-isoxazolyl | N(CH₃)₂ | 78–79 | 1 |
| 5-methyl-3-isoxazolyl | piperidino | 100–101 | 1 |
| 3-phenyl-5-methyl-4-isoxazolyl | NH₂ | 204–206 | 1 |
| 3-phenyl-5-methyl-4-isoxazolyl | N(CH₃)₂ | 117–119 | 1 |
| 3-phenyl-5-methyl-4-isoxazolyl | N(n-C₃H₇)₂ | 135–136 | 1 |
| 3-phenyl-5-methyl-4-isoxazolyl | piperidino | 133–135 | 1 |
| 3-phenyl-5-methyl-4-isoxazolyl | 1-azacyclooctyl | 127–219 | 1 |
| 3-phenyl-5-methyl-4-isoxazolyl | 1-(1,2,3,6-tetrahydropyridyl) | 127–129 | 1 |
| 4-methyl-5-oxazolyl | NH(n-C₃H₇) | 104–106 | 1 |
| 4-methyl-4-oxazolyl | N(CH₃)₂ | 120–123 | 1 |
| 4-methyl-5-oxazolyl | piperidino | 85–93 | 1 |
| 4-methyl-5-oxazolyl | 1-(1,2,3,6-tetrahydropyridyl) | 147–149 | 1 |
| 4-methyl-5-thiazolyl | NH(CH₃) | 173–174 | 1 |
| 4-methyl-5-thiazolyl | NH(C₂H₅) | 148–150 | 1 |
| 4-methyl-5-thiazolyl | NH(n-C₄H₉) | 103–104.5 | 1 |
| 4-methyl-5-thiazolyl | NH(CH₂)₅CH₃ | 99–100.5 | 1 |
| 4-methyl-5-thiazolyl | N(CH₃)₂ | 106–108 | 1 |
| 4-methyl-5-thiazolyl | N(C₂H₅)₂ | 72–75 | 1 |
| 4-methyl-5-thiazolyl | N(n-C₄H₉)₂ | 63–65 | 1 |
| 4-methyl-5-thiazolyl | piperidino | 103–105 | 1 |
| 4-methyl-5-thiazolyl | 1-(1,2,3,6-tetrahydropyridyl) | 129–132 | 1 |
| 5-isothiazolyl | NH₂ | 249–251 | 1 |
| 5-isothiazolyl | NH(CH₂)₅CH₃ | 103–105 | 1 |
| 5-isothiazolyl | N(CH₃)₂ | 112–114 | 1 |
| 5-isothiazolyl | piperidino | 144–146 | 1 |
| 5-isothiazolyl | 1-azacycloheptyl | 119–121 | 1 |
| 5-isothiazolyl | 1-(1,2,3,6-tetrahydropyridyl) | 142–143 | 1 |
| 3-isothiazolyl | NH₂ | 198–200 | 3 |
| 3-isothiazolyl | N(C₆H₅)₂ | 134–136 | 3 |
| 3-isothiazolyl | piperidino | 186–188 | 2 |
| 4-isothiazolyl | NH₂ | 252–253 | 1 |
| 4-isothiazolyl | NH(C₂H₅) | 171–172 | 1 |
| 4-isothiazolyl | N(CH₃)₂ | 181–182 | 1 |
| 4-isothiazolyl | N(n-C₃H₇)₂ | 130–131 | 1 |
| 4-isothiazolyl | NH(C₆H₁₁) | 115–116 | 1 |
| 4-isothiazolyl | piperidino | 155–156 | 1 |
| 4-isothiazolyl | morpholino | 142–143 | 1 |
| 4-isothiazolyl | 1-azacycloheptyl | 134–135 | 1 |
| 4-isothiazolyl | 1-(1,2,3,6-tetrahydropyridyl) | 132–133.5 | 1 |
| 3-methyl-5-isothiazolyl | NH₂ | 191–193 | 1 |
| 3-methyl-5-isothiazolyl | N(CH₃)₂ | 127–219 | 1 |
| 3-methyl-5-isothiazolyl | NH(CH₂)₅CH₃ | 123–125 | 1 |
| 3-methyl-5-isothiazolyl | piperidino | 137–139 | 1 |
| 3-methyl-5-isothiazolyl | 1-azacycloheptyl | 123–125 | 1 |
| 3-methyl-5-isothiazolyl | 1-(1,2,3,6-tetrahydropyridyl) | 154–155 | 1 |
| 5-methyl-1,2,3-thiadiazolyl | piperidino | 123–125 | 2 |
| 4-(1,2,3-thiadiazolyl) | NH(CH₂)₅CH₃ | 153–155 | 1 |
| 4-(1,2,3-thiadiazolyl) | N(CH₃)₂ | 179–181 | 1 |

| R | NR₁R₂ | M.P. (°C.) | Method of Example |
|---|---|---|---|
| 4-(1,2,3-thiadiazolyl) | piperidino | 157–159 | 1 |
| 4-(1,2,3-thiadiazolyl) | 1-(1,2,3,6-tetrahydropyridyl) | 136–138 | 1 |
| 4-(1,2,5-thiadiazolyl) | piperidino | 135–137 | 1 |
| 3-(benzisothiazolyl) | NH₂ | 174–176 | 1 |
| 3-(benzisothiazolyl) | N(CH₃)₂ | 152–154 | 1 |
| 3-(benzisothiazolyl) | piperidino | 116–118 | 1 |
| 3-(benzisothiazolyl) | 1-(1,2,3,6-tetrahydropyridyl) | 133–135 | 1 |
| 2-furyl | N(CH₃)₂ | 110–112 | 2 |
| 2-furyl | piperidino | 145–146 | 2 |
| 5-thiazolyl | N(n-C₄H₉)₂ | 63–65 | 2 |
| 2-chloro-3-pyridyl | NH(CH₂C₆H₅) | 190–191 | 1 |

(a) as hydrochloride
(b) as hydrate

EXAMPLE 5

Isonicotinoyl Urea

Urea (7.5 g., 0.125 mole) is suspended in liquid ammonia (250 ml.) in a round bottom flask fitted with an acetone/dry-ice condenser. Sodium pellets (2.9 g., 0.125 mole) are added and, after they have dissolved, methyl isonicotinate (12 g., 0.089 mole) is added to the mixture. The ammonia is allowed to evaporate from the mixture overnight. The yellow-tan residue is dissolved in water (150 ml.), the pH of the mixture adjusted to 5.5 with glacial acetic acid, and the precipitate which forms filtered, washed with water and air dired. It is then washed with hexane and triturated with boiling methanol. The white solid (isonicotinic acid) is removed by filtration and the filtrate evaporated to dryness to give the title product as a yellowish solid: m.p. 245°–247° C. Quantitative analysis and infra-red data are consistent with the values expected for the product.

EXAMPLE 6

The compounds tabulated below are prepared from appropriate reactants by the procedures of Examples 1–3 or 5.

| R | NR₁R₂ | Method of Example |
|---|---|---|
| 3-pyridyl | N(C₆H₅)₂ | 3 |
| 3-pyridyl | NH(C₃H₅) | 1 |
| 3-pyridyl | 4-methoxypiperidino | 1 |
| 3-pyridyl | 4-n-butoxypiperidino | 1 |
| 3-pyridyl | 3-chloropiperidino | 1 |
| 4-pyridyl | NH(C₆H₅) | 1 |
| 4-pyridyl | N(C₆H₅)₂ | 2 |
| 4-pyridyl | N[(CH₂)₉CH₃]₂ | 1 |
| 4-pyridyl | NH(CH₂C₆H₅) | 2 |
| 4-pyridyl | NH[(CH₂)₄C₆H₅] | 1 |
| 4-pyridyl | N(CH₃)(C₆H₅) | 1 |
| 4-pyridyl | N(n-C₃H₇)(CH₂C₆H₅) | 2 |
| 4-pyridyl | morpholino | 1 |
| 4-pyridyl | thiomorpholino | 1 |
| 4-pyridyl | NH(1-naphtyl) | 1 |
| 4-pyridyl | 4-methylpiperidino | 1 |
| 4-pyridyl | 2-ethoxypiperidino | 1 |
| 4-pyridyl | 4-n-propylpiperidino | 2 |
| 4-pyridyl | 4-chloropiperidino | 2 |
| 4-pyridyl | 4-(3-phenylpropyl)piperidino | 1 |
| 4-pyridyl | 3-(2,3,4,5-tetrahydro-3,1-benzazepinyl) | 1 |
| 5-chloro-3-pyridyl | NH₂ | 1 |
| 5-chloro-3-pyridyl | N(CH₃(C₆H₅) | 2 |
| 5-chloro-3-pyridyl | N(CH₃)(n-C₄H₉) | 2 |
| 5-chloro-3-pyridyl | N(CH₃)(CH₂C₆H₅) | 1 |
| 5-chloro-3-pyridyl | N(C₆H₅)₂ | 3 |
| 5-chloro-3-pyridyl | piperidino | 3 |
| 5-chloro-3-pyridyl | 2-chloropiperidino | 3 |
| 5-chloro-3-pyridyl | 4-ethylpiperidino | 3 |
| 5-chloro-3-pyridyl | 4-benzylpiperidino | 1 |
| 5-chloro-3-pyridyl | NH(CH₂)₈CH₃ | 2 |
| 5-chloro-3-pyridyl | 4-ethoxypiperidino | 1 |
| 5-chloro-3-pyridyl | morpholino | 1 |
| 5-chloro-3-pyridyl | thiomorpholino | 1 |
| 5-chloro-3-pyridyl | 1-azacyclooctyl | 2 |
| 5-chloro-3-pyridyl | NH(C₄H₇) | 1 |
| 5-chloro-3-pyridyl | N(CH₃(C₆H₁₁) | 1 |

-continued $$R-\overset{O}{\underset{\|}{C}}-NH-\overset{O}{\underset{\|}{C}}-N\overset{R_1}{\underset{R_2}{}}$$

| R | NR₁R₂ | Method of Example |
|---|---|---|
| 5-chloro-3-pyridyl | NH(1-naphthyl) | 2 |
| 2-chloro-3-pyridyl | NH(C$_6$H$_5$) | 1 |
| 2-chloro-3-pyridyl | N(CH$_3$)C$_6$H$_5$ | 1 |
| 2-chloro-3-pyridyl | N(n-C$_3$H$_7$)(CH$_2$C$_6$H$_5$) | 1 |
| 2-chloro-3-pyridyl | N[(CH$_2$)$_5$CH$_3$]$_2$ | 2 |
| 2-chloro-3-pyridyl | N(CH$_3$)(C$_6$H$_{11}$) | 2 |
| 2-chloro-3-pyridyl | 4-(4-phenylbutyl)piperidino | 1 |
| 2-chloro-3-pyridyl | 1-azacycloheptyl | 3 |
| 2-chloro-3-pyridyl | morpholino | 3 |
| 2-chloro-3-pyridyl | 4-methoxypiperidino | 1 |
| 2-chloro-3-pyridyl | N(n-C$_6$H$_{13}$)CH$_2$C$_6$H$_5$ | 1 |
| 2-chloro-3-pyridyl | NH(1-naphthyl) | 2 |
| 2-chloro-3-pyridyl | 4-n-butylpiperidino | 3 |
| 2-chloro-3-pyridyl | 2-methoxypiperidino | 1 |
| 2-pyridyl | NH$_2$ | 5 |
| 2-pyridyl | NH(CH$_3$) | 1 |
| 2-pyridyl | NH[(CH$_2$)$_9$CH$_3$] | 1 |
| 2-pyridyl | NHC$_6$H$_5$ | 1 |
| 2-pyridyl | NH(CH$_2$C$_6$H$_5$) | 2 |
| 2-pyridyl | N(CH$_3$)(CH$_2$C$_6$H$_5$) | 2 |
| 2-pyridyl | N(n-C$_3$H$_7$)(C$_6$H$_5$) | 1 |
| 2-pyridyl | NH(C$_6$H$_{11}$) | 2 |
| 2-pyridyl | NH-(1-naphthyl) | 1 |
| 2-pyridyl | N(CH$_3$)(1-naphthyl) | 1 |
| 2-pyridyl | N(n-C$_4$H)(1-naphthyl) | 1 |
| 2-pyridyl | N(CH$_3$)(n-C$_6$H$_{13}$) | 1 |
| 2-pyridyl | N(CH$_3$)(C$_6$H$_{11}$) | 1 |
| 2-pyridyl | piperidino | 2 |
| 2-pyridyl | 3-ethylpiperidino | 1 |
| 2-pyridyl | 3-n-propoxypiperidino | 1 |
| 2-pyridyl | thiomorpholino | 2 |
| 2-pyridyl | 2-chloropiperidino | 1 |
| 2-pyridyl | 4-benzylpiperidino | 1 |
| 2-pyridyl | 1-(1,2,3,6-tetrahydropyridyl) | 1 |
| 3-quinolyl | NH$_2$ | 5 |
| 4-quinolyl | 1-(1,2,3,6-tetrahydropyridyl) | 1 |
| 5-quinolyl | 1-(1,2,3,6-tetrahydropyridyl) | 1 |
| 6-quinolyl | 1-(1,2,3,6-tetrahydropyridyl) | 1 |
| 7-quinolyl | 1-(1,2,3,6-tetrahydropyridyl) | 1 |
| 8-quinolyl | 1-(1,2,3,6-tetrahydropyridyl) | 1 |
| 5-quinolyl | NH$_2$ | 5 |
| 8-quinolyl | NH$_2$ | 5 |
| 4-quinolyl | NH(CH$_2$C$_6$H$_5$) | 1 |
| 4-quinolyl | NH(CH$_2$)$_9$CH$_3$ | 1 |
| 4-quinolyl | N(n-C$_4$H$_9$)$_2$ | 5 |
| 2-quinolyl | NH(CH$_2$C$_6$H$_5$) | 1 |
| 2-quinolyl | NH$_2$ | 5 |
| 2-quinolyl | 1-(1,2,3,6-tetrahydropyridyl) | 1 |
| 2-quinolyl | NH[(CH$_2$)$_9$CH$_3$] | 1 |
| 5-quinolyl | piperidino | 1 |
| 6-quinolyl | N(CH$_3$)(C$_6$H$_{11}$) | 1 |
| 6-quinolyl | 1-azacyclooctyl | 1 |
| 7-quinolyl | N(n-C$_4$H$_9$)$_2$ | 1 |
| 3-methyl-5-isoxazolyl | NH(C$_5$H$_9$) | 1 |
| 3-methyl-5-isoxazolyl | N(CH$_3$)(n-C$_7$H$_{15}$) | 1 |
| 3-methyl-5-isoxazolyl | N(C$_2$H$_5$)(C$_6$H$_5$) | 1 |
| 3-methyl-5-isoxazolyl | N(n-C$_3$H$_7$)(C$_6$H$_{11}$) | 2 |
| 3-methyl-5-isoxazolyl | 4-(2-phenylethyl)piperidino | 1 |
| 3-methyl-5-isoxazolyl | 3-ethoxypiperidino | 1 |
| 5-methyl-3-isoxazolyl | NH$_2$ | 5 |
| 5-methyl-3-isoxazolyl | morpholino | 1 |
| 5-methyl-3-isoxazolyl | NH(CH$_2$C$_6$H$_5$) | 1 |
| 5-methyl-3-isoxazolyl | N[(CH$_2$)$_2$CH(CH$_3$)$_2$]$_2$ | 1 |
| 5-methyl-3-isoxazolyl | 1-(1,2,3,6-tetrahydropyridyl) | 1 |
| 5-methyl-3-phenyl-4-isoxazolyl | thiomorpholino | 2 |
| 5-methyl-3-phenyl-4-isoxazolyl | NH[(CH$_2$)$_6$CH$_3$] | 3 |
| 5-methyl-3-phenyl-4-isoxazolyl | N(C$_6$H$_5$)$_2$ | 1 |
| 5-methyl-3-phenyl-4-isoxazolyl | NH(C$_3$H$_5$) | 1 |
| 5-methyl-3-phenyl-4-isoxazolyl | N(n-C$_4$H$_9$(CH$_2$C$_6$H$_5$) | 1 |
| 5-methyl-3-phenyl-4-isoxazolyl | 3-methylpiperidino | 1 |
| 4-methyl-5-oxazolyl | NH$_2$ | 5 |
| 4-methyl-5-oxazolyl | NH(C$_6$H$_{11}$) | 5 |
| 4-methyl-5-oxazolyl | N(C$_2$H$_5$)(C$_6$H$_5$) | 1 |
| 4-methyl-5-oxazolyl | N(n-C$_4$H$_9$)(CH$_2$C$_6$H$_5$) | 2 |
| 4-methyl-5-oxazolyl | 3-chloropiperidino | 2 |
| 4-methyl-5-oxazolyl | N(C$_5$H$_9$)(CH$_3$) | 1 |

-continued $$R-\overset{O}{\underset{\|}{C}}-NH-\overset{O}{\underset{\|}{C}}-N\overset{R_1}{\underset{R_2}{\diagdown}}$$

| R | NR₁R₂ | Method of Example |
|---|---|---|
| 4-methyl-5-oxazolyl | 1-azacycloheptyl | 1 |
| 4-methyl-5-oxazolyl | 4-(3-phenylpropyl)piperidino | 1 |
| 4-methyl-5-oxazolyl | NH(1-naphthyl) | 1 |
| 4-methyl-5-thiazolyl | NH₂ | 5 |
| 4-methyl-5-thiazolyl | N[(CH₂)₅CH₃]₂ | 1 |
| 4-methyl-5-thiazolyl | N(CH₃)(i-C₃H₇) | 1 |
| 4-methyl-5-thiazolyl | N(C₆H₅)₂ | 3 |
| 4-methyl-5-thiazolyl | N(n-C₄H₉)(CH₂C₆H₅) | 1 |
| 4-methyl-5-thiazolyl | 4-ethylpiperidino | 1 |
| 5-isothiazolyl | N(n-C₄H₉)₂ | 3 |
| 5-isothiazlyl | 3-n-propoxypiperidino | 1 |
| 5-isothiazolyl | NH(C₆H₁₁) | 1 |
| 5-isothiazolyl | N(C₆H₅)(CH₂C₆H₅) | 1 |
| 3-isothiazolyl | N(CH₃)(n-C₆H₁₃) | 1 |
| 3-isothiazolyl | N(CH₃)(n-C₁₀H₂₁) | 1 |
| 3-isothiazolyl | morpholino | 1 |
| 3-isothiazolyl | N(n-C₄H₉)₂ | 1 |
| 3-isothiazolyl | N(C₂H₅)(CH₂C₆H₅) | 1 |
| 4-isothiazolyl | N(C₆H₅)₂ | 2 |
| 4-isothiazolyl | NH(1-naphthyl) | 2 |
| 4-isothiazolyl | NH(C₆H₁₁) | 1 |
| 4-isothiazolyl | N(C₆H₅)(C₆H₁₁) | 1 |
| 4-isothiazolyl | NH[C(CH₃)₃] | 1 |
| 3-methyl-5-isothiazolyl | NHCH₂C₆H₅ | 1 |
| 3-methyl-5-isothiazolyl | N(CH₃)(C₆H₅) | 1 |
| 3-methyl-5-isothiazolyl | N[(CH₂)₉CH₃]₂ | 2 |
| 3-methyl-5-isothiazolyl | 4-(4-phenylbutyl)piperidino | 1 |
| 3-methyl-5-isothiazolyl | NH(C₄H₇) | 2 |
| 3-methyl-5-isothiazolyl | N(C₂H₅)(n-C₆H₁₃) | 1 |
| 3-methyl-5-isothiazolyl | morpholino | 1 |
| 3-methyl-5-isothiazolyl | 1-azacycloheptyl | 1 |
| 3-methyl-5-isothiazolyl | 3-chloropiperidino | 1 |
| 4-(1,2,3-thiadiazolyl) | NH₂ | 5 |
| 4-(1,2,3-thiadiazolyl) | NH(n-C₄H₉) | 5 |
| 4-(1,2,3-thiadiazolyl) | NH(CH₂C₆H₅) | 1 |
| 4-(1,2,3-thiadiazolyl) | N(C₆H₅)₂ | 1 |
| 4-(1,2,3-thiadiazolyl) | N(CH₃)(C₆H₁₁) | 1 |
| 3-(1,2,5-thiadiazolyl) | NH₂ | 5 |
| 3-(1,2,5-thiadiazolyl) | N(n-C₄H₉)₂ | 1 |
| 3-(1,2,5-thiadiazolyl) | 1-(1,2,3,6-tetrahydropyridyl) | 1 |
| 3-(1,2,5-thiadiazolyl) | 4-(n-propoxy)piperidino | 1 |
| 3-(1,2,5-thiadiazolyl) | N(i-C₃H₇)₂ | 1 |
| 3-(1,2,5-thiadiazolyl) | NH(C₃H₅) | 1 |
| 3-benzisothiazolyl | N[(CH₂)₂CH(CH₃)₂]₂ | 1 |
| 3-benzisothiazolyl | N(C₆H₅)(n-C₄H₉) | 1 |
| 3-benzisothiazolyl | N(CH₃)(C₆H₁₁) | 1 |
| 3-benzisothiazolyl | 4-methylpiperidino | 1 |
| 3-benzisothiazolyl | NH(1-naphthyl) | 2 |
| 2-benzisothiazolyl | 1-azacyclooctyl | 1 |
| 3-benzisothiazolyl | morpholino | 1 |
| 3-benzisothiazolyl | 4-chloropiperidino | 1 |
| 2-furyl | NH₂ | 5 |
| 2-furyl | N(CH₃)(n-C₆H₁₃) | 1 |
| 2-furyl | NH(CH₂)₉CH₃ | 1 |
| 2-furyl | 1-(1,2,3,6-tetrahydropyridyl) | 1 |
| 2-furyl | 4-(3-phenylpropyl)piperidino | 1 |
| 2-furyl | N(C₂H₅)(C₆H₁₁) | 2 |
| 2-furyl | N(C₆H₅)₂ | 2 |
| 2-furyl | N(CH₃)(CH₂C₆H₅) | 1 |
| 2-furyl | NH(1-naphthyl) | 1 |
| 3-furyl | NH₂ | 5 |
| 3-furyl | N(n-C₄H₉)₂ | 1 |
| 3-furyl | 1-(1,2,3,6-tetrahydrpyridyl) | 1 |
| 3-furyl | piperidino | 1 |
| 3-furyl | thiomorpholino | 1 |
| 3-furyl | 2-chloropiperidino | 2 |
| 3-furyl | 2-methylpiperidino | 2 |
| 3-furyl | N(n-C₄H₉)(C₆H₅) | 2 |
| 4-pyridyl | NH₂ | 5 |
| 2-chloro-3-pyridyl | 4-(4-chlorophenyl)piperidino | 1 |
| 4-pyridyl | 4-(4-chlorophenyl)piperidino | 1 |
| 3-quinolyl | 4-(2-chlorophenyl)piperidino | 1 |
| 3-methyl-5-isoxazolyl | 4-(4-chlorophenyl)piperidino | 1 |
| 5-methyl-3-isoxazolyl | 4-(4-chlorophenyl)piperidino | 1 |
| 3-(1,2,5-thiadiazolyl) | 4-(4-chlorophenyl)piperidino | 1 |
| 5-thiazolyl | 1-(1,2,3,6-tetrahydropyridyl) | 1 |

-continued

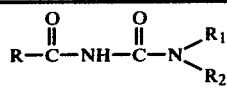

| R | NR₁R₂ | Method of Example |
|---|---|---|
| 5-thiazolyl | NH(CH₂C₆H₅) | 1 |
| 5-thiazolyl | 1-azacyclooctyl | 1 |
| 5-thiazolyl | NH[(CH₂)₄C₆H₅] | 1 |
| 4-thiazolyl | NH(CH₂C₆H₅) | 1 |
| 4-thiazolyl | 1-(1,2,3,6-tetrahydropyridyl) | 1 |
| 4-thiazolyl | NH(CH₂)₉CH₃ | 1 |
| 4-thiazolyl | N(CH₃)(C₆H₅) | 1 |
| 4-thiazolyl | piperidino | 1 |
| 5-thiazolyl | 4-(3-phenylpropyl)piperidino | 1 |

General Methods for Preparation of Amide Reactants

Method A

The appropriate acid reactant of formula R—COOH is heated to reflux in an excess of thionyl chloride for 3 hours. The reaction mixture is then evaporated to dryness under reduced pressure and the residue added in small portions with stirring to an excess of concentrated ammonium hydroxide at room temperature. The mixture is stirred for one hour following completion of addition and the product recovered by filtration if it is insoluble or by evaporation if it is soluble.

Method B

The appropriate nitrile reactant of formula R—CN is added to ethanol containing a 10% excess of potassium hydroxide. To the resulting mixture is added excess 30% hydrogen peroxide and the reaction mixture heated gently to 60° C. The reaction becomes exothermic and is cooled if necessary to maintain the temperature at about 60° C. The reaction is allowed to continue until oxygen evolution ceases. It is then concentrated under reduced pressure to small volume, the residue filtered, washed with water and dried.

What is claimed is:

1. A method of dissolving cholesterol gallstones in a mammal which comprises administering to the mammal a cholesterol gallstone dissolving amount of a compound having the formula

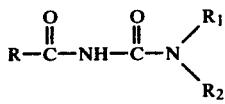

wherein R is selected from the group consisting of
pyridyl,
chloro substituted pyridyl,
quinolyl,
furyl,
5-methyl-3-isoxazolyl,
3-methyl-5-isoxazolyl,
3-methyl-5-isothiazolyl,
4-methyl-5-thiazolyl,
4-methyl-5-oxazolyl,
5-methyl-3-phenyl-4-isoxazolyl,
isothiazolyl,
3-(1,2,5-thiadiazolyl),
4-(1,2,3-thiadiazolyl),
3-(1,2-benzisothiazolyl) and
thiazolyl:
R₁ is selected from the group consisting of hydrogen, alkyl having from one to ten carbon atoms and phenyl;
R₂ is selected from the group consisting of R₁, 1-naphthyl and phenylalkyl wherein the alkyl has from one to four carbon atoms;
R₁ and R₂ when taken together with the nitrogen to which they are attached are selected from the group consisting of
morpholino,
thiomorpholino,
1-(1,2,3,6-tetrahydropyridyl),
1-azacycloheptyl,
1-azacyclooctyl,
3-(2,3,4,5-tetrahydro-3,1-benzazepinyl) and

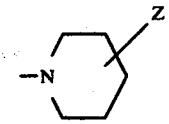

wherein Z is selected from the group consisting of hydrogen, alkyl having from one to four carbon atoms, alkoxy having from one to four carbon atoms, chloro and phenylalkyl having from one to four carbon atoms in the alkyl group, and the pharmaceutically acceptable acid addition salts of those compounds wherein R is a basic group.

2. The method according to claim 1 wherein in the formula for the compound, R₁ and R₂ together with the nitrogen to which they are attached represent 1-(2,3,4,6-tetrahydropyridyl).

3. The method according to claim 2 wherein R is chloro substituted pyridyl.

4. The method according to claim 3 wherein R is 5-chloro-3-pyridyl.

5. The method according to claim 2 wherein R is 3-quinolyl.

6. The method according to claim 1 wherein R₁ is hydrogen and R₂ is benzyl.

7. The method according to claim 6 wherein R is 3-pyridyl.

8. The method according to claim 6 wherein R is 2-chloro-3-pyridyl.

9. The method according to claim 1 wherein R is 4-methyl-5-thiazolyl and each of R₁ and R₂ is n-butyl.

10. The method according to claim 1 wherein R is 6-chloro-3-pyridyl and NR₁R₂ is thiomorpholino.

* * * * *